(12) United States Patent
Venaas

(10) Patent No.: US 8,978,446 B2
(45) Date of Patent: Mar. 17, 2015

(54) METHOD AND APPARATUS FOR MEASURING METAL PORTION IN DROSS

(75) Inventor: Karl Venaas, Haslum (NO)

(73) Assignee: ALU Innovation AS, Trondheim (NO)

( * ) Notice: Subject to any disclaimer, the term of this patent is extended or adjusted under 35 U.S.C. 154(b) by 785 days.

(21) Appl. No.: 13/061,201

(22) PCT Filed: Aug. 19, 2009

(86) PCT No.: PCT/NO2009/000292
§ 371 (c)(1),
(2), (4) Date: Apr. 21, 2011

(87) PCT Pub. No.: WO2010/027267
PCT Pub. Date: Mar. 11, 2010

(65) Prior Publication Data
US 2011/0197670 A1    Aug. 18, 2011

(30) Foreign Application Priority Data
Sep. 2, 2008  (NO) .................................. 20083781

(51) Int. Cl.
| | |
|---|---|
| *G01N 9/00* | (2006.01) |
| *G01N 9/36* | (2006.01) |
| *G01N 15/08* | (2006.01) |
| *G01N 33/20* | (2006.01) |

(52) U.S. Cl.
CPC ................ *G01N 9/36* (2013.01); *G01N 15/088* (2013.01); *G01N 33/20* (2013.01)
USPC ....................................................... 73/32 R

(58) Field of Classification Search
None
See application file for complete search history.

(56) References Cited

U.S. PATENT DOCUMENTS 6,637,265 B1    10/2003    Hay, Jr. et al.

FOREIGN PATENT DOCUMENTS

| | | |
|---|---|---|
| JP | 9178641 | 7/1997 |
| WO | 0120300 | 3/2001 |

OTHER PUBLICATIONS

Micromeritics Instrument Corporation, AccuPyc 1330 Pycnometer Operator's Manual, Sep. 1996, Micromeritics InstrumentCorporation, V3.03, 1-2, 1-3, 3-2, 3-4, 3-5, B-1, B-2, B-3; C-1.*

* cited by examiner

*Primary Examiner* — Peter Macchiarolo
*Assistant Examiner* — Nathaniel Kolb
(74) *Attorney, Agent, or Firm* — Ladas & Parry LLP

(57) ABSTRACT

Method and apparatus for determination of portion of pure metal in dross from a dross source, whereby the metal portion in the dross is determined by measuring the dross density and calculating the metal portion in accordance with the formula m%=k–ρ+a, where m% is percentage pure metal, ρ is the dross density and k and a are empirical constants. In accordance with the invention, the apparatus comprises a closed container (1) for dross provided with temperature gauge (9), pressure gauge (8) and an outlet pipe (18) having a valve (12) for removal of gas from the dross container (1), a closed container (2) for gas provided with a valve (14) for supplying gas from a gas source (16) to the gas container (2), whereby the dross container (1) and the gas container (2) are in a flow connection via a pipe (20).

3 Claims, 1 Drawing Sheet

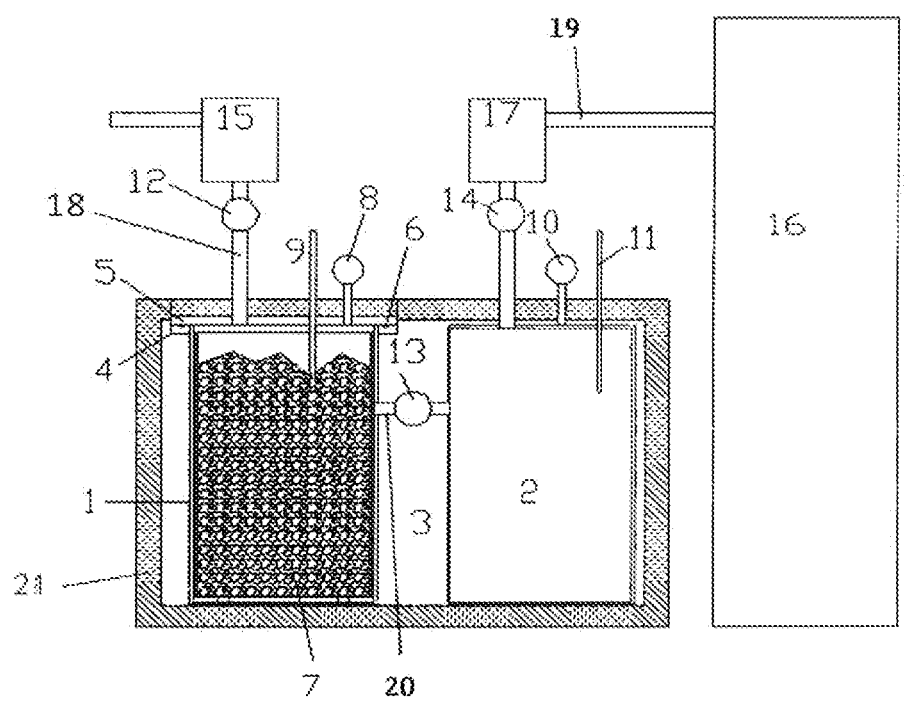

METHOD AND APPARATUS FOR MEASURING METAL PORTION IN DROSS

BACKGROUND OF THE INVENTION

The invention concerns a method and apparatus for measuring metal portion in dross from a dross source.

Dross is formed during production, refinement, alloying and casting of metal, whereby liquid metal reacts with oxygen in air and forms oxides, or from gas treatment, addition of fluxing material, alloying elements or similar. With regard to aluminum, the dross normally comprises from 40 to 90% metallic aluminum, 15 to 45% aluminum oxide and the remainder cryolite, carbides, nitrides, spinel etc.

For example during production and casting of aluminum, a relatively large amount of dross is formed, typically from 0.5 to 10% dross. This dross is withdrawn from the melting furnace at a high temperature, for example 600-800° C., and is in some cases transferred to cooling containers, to dross compressing device for extortion of molten metal, or to an open container for cooling.

In the smelting industry, the dross constitutes a considerable value, and is often sold to other industry parties for extraction of the metal from the dross. During production, dross from numeral furnaces is cooled down and collected in large piles prior to shipping to customer. In order to put as most correct dross price as possible, it is important to know the metal portion in the dross. Since the dross has substantially the same appearance regardless of the metal portion, for example 10% versus 70%, a physical/chemical analysis of the dross must be performed in order to quantify the metal portion.

This can be performed by taking samples of the dross in the dross piles, whereby the metal portion is determined by measuring density with a pycnometer or similar at room temperature and substantially atmospheric pressure. However, this method is highly uncertain because the metal portion varies largely from one furnace to another and even from one operator to another with regard to dross from the same furnace.

Accordingly, there is a need to obtain a more accurate determination of the metal portion in dross, both with regard to quantification of metal portion in dross sold to other enterprises or with regard to the melting process control in order to optimize the process yield.

From the applicant's own WO patent publication 01/20300 it is known that there is a linear relationship between the metal portion in dross and the dross density, represented by the formula $$m\% = k \cdot \rho + a,$$

where m% is percent pure metal, $\rho$ is the dross density, and k and a are empirical constants. However, prior art measurement methods require the sample is cooled down prior to measurement, and it is typically necessary to spend hours to obtain the result of the analysis. However, it is very difficult to control the process parameter with this method in order to control the metal portion in dross and quantify the metal portion with regard to sale of dross to other parties or for use in other processes.

JP patent publication 9178641 describes a method and a container for measuring density of molten metal. A closed container is used, keeping the liquid metal at constant temperature. A sleeve is partly immersed in the liquid metal to form two separate chambers inside and outside the sleeve, respectively. Pressurized inert gas is supplied to the container outside the sleeve, thus establishing a level difference of the metal surface between the interior and exterior of the sleeve. This level difference is, together with the gas pressure inside and outside the sleeve above the metal surfaces, used to calculate the density of the molten metal. However, this technique cannot be used to measure metal in the dross.

SUMMARY OF THE INVENTION

An objective of the invention is to provide a method and apparatus to determine the metal portion in dross from a dross source, which enables a fast and accurate qualitative and quantitative determination of metal in the dross.

In accordance with one aspect of the present invention, it is provided a method and apparatus for determination of portion pure metal in dross from a dross source, whereby the metal portion in the dross is determined by measuring the dross density and calculating the metal portion in accordance with the formula m%=k·$\rho$+a, where m% is percent pure metal, $\rho$ is dross density and k and a are empirical constants, whereby the density is determined by:

transferring dross having known mass from the dross source to a closed container having a known volume, closing the dross container and evacuating gas from the same, supplying an inert gas to the closed container, reading the amount of gas supplied to the container.

In accordance with the invention, the dross is transferred to a closed container system comprising a sample container for reception of the dross sample, and a gas container containing inert gas, whereby the dross is supplied to the sample container without cooling.

This enables a very fast and not at least accurate determination of the metal portion in the dross. The method is fast because dross can be transferred directly from a melting furnace, for example, to the dross container, and it is not necessary to wait for a time-consuming cooling process. By making measurements of the metal portion in dross taken from the dross source repeatedly, it is therefore possible to obtain a very accurate value for the metal portion in dross, which is sold to other industry parties or is used in other processes. Another benefit is that the fast determination enables adjustment of the process parameters, thus controlling the metal portion in the dross.

The inert gas is preferably preheated to a temperature substantially equal to the temperature of the dross from the dross source to obtain more accurate results.

Another benefit by performing determination of the metal portion at high temperature is that the micropores in the dross are expanded as a result of the high temperature. In this way the inert gas will penetrate the pore volume to a greater extent and provide a more accurate determination of the free volume versus the dross volume at the pressure and temperature in question, which again provides a more accurate determination of the metal portion.

Any gas which does not react with the dross material can be used. Hydrogen is the gas having the smallest molecular size of all gases and would be the gas which would establish the highest degree of penetration in the dross and for that reason highest accuracy. But hydrogen is as known connected with practical disadvantages because of the explosive reactivity with oxygen, and in many cases it can be appropriate to use different gases. A preferred gas is helium because of its small molecular size (the double size of hydrogen) and substantially ideal character (approximately ideal gas). It is also possible to utilize air or nitrogen, for example, but this is less preferred because the gases because of their relatively large molecular size will not exhibit a sufficient penetration into the dross pore volume and will provide measured dross density with a higher error margin.

The method and apparatus in accordance with the present invention can result in large economical savings. For example, the annual production of aluminum in Norway is about 1.5 million tons. About 2% of the metal is lost with the dross. By using the present invention it is possible to reduce the loss to, for example, 1% by controlling the process parameters in the melting process from density measurements and metal portion in the dross. With a market price of NOK 20 000/ton Al it is possible to obtain a saving of NOK 300 million.

BRIEF DESCRIPTION OF THE DRAWING

The invention is in the following described in further detail with reference to the sole drawing FIGURE, which illustrates an embodiment of an apparatus in accordance with the present invention to practice the method in accordance with the present invention.

DESCRIPTION OF THE PREFERRED EMBODIMENTS

FIG. 1 illustrates strongly schematically an embodiment of an apparatus in accordance with the invention for determination the portion of pure metal in dross. The apparatus comprises a dross container 1 for dross 7 and a gas container 2. Both containers are located within a chamber 3 provided with a heating device (not illustrated). The sample chamber 3 is preferably formed of a heat insulating material 21. The dross container 1 is provided with a flange 4 at the top of the same for reception of a lid 5. The lid is constructed for attachment to the flange 4 with bolts or similar. A gasket 6 is arranged between the flange 4 and the lid 5 to establish a gas tight connection.

The dross container is provided with a temperature gauge 9 and a pressure gauge 8 for metering of temperature and pressure inside the container, respectively, and a pipe 18 for removal of gas from the gas container 1. The gas pipe 18 is provided with a valve 12 and a check valve 15 to prevent gas from flowing back to the dross container. The gas container 2 is in a flow connection with the dross container 1 via a gas pipe 20 provided with a valve 13.

The gas container 2 is, equal to the gas container 1, provided with a temperature gauge 11 and pressure gauge 10. A gas pipe 19 is connected with the gas container for supply of gas from a gas source 16. The gas pipe 19 is provided with a valve 14 and a gas heater 17.

During sampling the operator takes a sample from the dross source and places the sample in a bucket (not shown). The bucket is weighed and placed into the dross container 1. The dross container is closed whereupon the valve 13 between the gas container 2 and dross container 1 is closed. The valve 12 in the outlet pipe is opened, and the dross container 1 is evacuated by means of a vacuum pump (not shown) whereupon the valve 12 is closed. Then the gas container 2 is supplied with gas from the gas source 16 at a pressure above atmospheric, such as about 2 bar. The gas is heated by the gas heater 17 to a temperature close to the dross temperature. The chamber 3 is preferably also heated to the same temperature as the dross. Then the operator measures the pressure $P_2$ and temperature $T_2$ in the gas container 2, whereupon the operator opens the valve 13 between the dross container and the gas container, so that gas flows from the gas container to the dross container until the pressure is equalized. When the pressure has been equalized, pressure and temperature is measured in the respective containers: $P_1$, $T_1$, $P_2$, $T_2$. In the end, the valve 13 between the containers is closed and the pressure in the dross container is reduced to atmospheric by opening the valve 12 in the outlet pipe 18 for the dross container.

Since the volume of the respective containers is known, we have sufficient information to determine the dross density and then the portion of pure metal in the same. With basis in the equation for the ideal gases (1), the equation for the relationship between mol and mass (2), and the equation for density (3), we are able to calculate the dross density by means of the measured values for mass, pressure and temperature and by means of equation (4):

$$P \cdot V = n \cdot R \cdot T \quad (1)$$

$$n = m/M \quad (2)$$

$$\rho = m/V \quad (3)$$

$$\rho = P \cdot M/(R \cdot T) \quad (4)$$

where P=pressure (bar), V=volume ($dm^3$), n=number of mol gas, R=the gas constant (0.08314 bar·$dm^3$/(mol·° K), m=the mass of the dross sample (grams), M=gas molecular weight (g/mol) and $\rho$=dross density (g/$cm^3$). The calculated portion for the dross density is then used in equation (5) below to determine the portion of pure metal in the dross sample:

$$m\% = k \cdot \rho + a \quad (5)$$

wherein the constants k and a have been determined in advance in accordance with the prior art as stated in the prior art section:
 k=−103,71
 a=366,57
Accordingly, the percentage aluminum in dross is determined in accordance with the formula $$m\% = -103.71 * \rho + 366.57$$

A density measurement of aluminum was made in accordance with the method described above to constitute 3.0788 g/$dm^3$, which gave a percentage of pure aluminum in the dross as follows:

$$m\% = -103.71 * 3.0788 + 366.57 = 47.27\% \text{ Al}$$

Accordingly, the present invention enables determination of the portion of pure metal in dross from dross sources, such as melting furnaces, during a short period of time. The analysis method in accordance with the present invention can typically be made within 15 minutes, whereas the prior art needs several hours to complete. Moreover, the method and apparatus in accordance with the present invention enables use of the analysis result to control the melting process by adjusting the process parameters, for example, in order to reduce the portion of pure metal in the dross.

Whereas the present invention has been described with only one of its embodiments, a person skilled in the art will quickly realize that the apparatus can be provided in numerous variants without deviating from the scope of the invention. The description above is highly schematic, and the method has been described as batchwise. However, the invention is not limited to this and the method can easily be made continuous and automated.

What is claimed is:

1. A method for determining portion of pure metal in dross from a dross source, whereby the metal portion is determined by measuring the dross density and calculating the metal portion in accordance with the formula m%=k·$\rho$+a, wherein m% is percentage pure metal, ρ is dross density, and k and a are empirical constants, whereby the density is determined by:

- transferring dross having known mass from the dross source to a closed container having a known volume,
- closing the dross container and evacuating gas from the dross container,
- supplying a gas to the closed container,
- reading the amount of gas supplied to the closed container, wherein the dross having a temperature of up to 600 to 800° C. is transferred to a closed container system comprising the dross container and a gas container containing an inert gas, wherein the method further comprises the following steps:
- supplying a gas at a pressure above atmospheric pressure to the gas container;
- closing the gas container;
- measuring temperature and pressure inside the closed gas container;
- opening a gas line between the closed gas container and the closed dross container;
- allowing the pressure between the dross container and gas container to become equalized; and
- measuring the temperature and pressure of the dross container and the gas container before opening the dross container to the atmosphere; and then
- calculating the dross density and the portion of pure metal in the dross.

2. The method of claim 1, wherein the gas in the gas container is preheated to a temperature substantially equal to the dross temperature.

3. The method of claim 1, wherein the gas is helium.

* * * * *